(12) United States Patent
Kouno et al.

(10) Patent No.: US 8,221,372 B2
(45) Date of Patent: Jul. 17, 2012

(54) DISPOSABLE DIAPER HAVING FOLDED FRONT-SIDED END FLAP PORTION

(75) Inventors: Shinichi Kouno, Shikokuchuo (JP); Tsuyoshi Utsunomiya, Shikokuchuo (JP); Sadanao Manabe, Shikokuchuo (JP); Toshikazu Maeda, Shikokuchuo (JP); Yumiko Seike, Shikokuchuo (JP); Miyuke Ochi, Shikokuchuo (JP)

(73) Assignee: Daio Paper Corporation, Shikokuchuo-shi, Ehime (JP)

( * ) Notice: Subject to any disclaimer, the term of this patent is extended or adjusted under 35 U.S.C. 154(b) by 757 days.

(21) Appl. No.: 11/922,452

(22) PCT Filed: Jun. 15, 2006

(86) PCT No.: PCT/JP2006/312044
§ 371 (c)(1),
(2), (4) Date: Dec. 17, 2007

(87) PCT Pub. No.: WO2006/135011
PCT Pub. Date: Dec. 21, 2006

(65) Prior Publication Data
US 2009/0105682 A1    Apr. 23, 2009

(30) Foreign Application Priority Data

Jun. 15, 2005 (JP) .................. 2005-175334
Jun. 15, 2005 (JP) .................. 2005-175338
Aug. 26, 2005 (JP) .................. 2005-245778

(51) Int. Cl.
*A61F 13/15* (2006.01)
*A61F 13/20* (2006.01)

(52) U.S. Cl. ....... 604/385.04; 604/385.201; 604/385.29; 604/385.3; 604/400

(58) Field of Classification Search ............. 604/385.04, 604/385.201, 385.29, 385.3, 400
See application file for complete search history.

(56) References Cited

U.S. PATENT DOCUMENTS
3,089,494 A * 5/1963 Schwartz ................ 604/389
(Continued)

FOREIGN PATENT DOCUMENTS
JP            5-192368         8/1993
(Continued)

*Primary Examiner* — Tatyana Zalukaeva
*Assistant Examiner* — Ginger T Chapman
(74) *Attorney, Agent, or Firm* — Jordan and Hamburg LLP

(57) ABSTRACT

Provided is a disposable diaper, in which fastening tapes are brought into direct engagement with the surface of an outer-face back sheet made of a nonwoven fabric. The disposable diaper is enabled to adjust its size slightly according to the body shape of a baby, by improving the force of the fastening tapes to engage with the outer-face back sheet and the force to join the outer-face back sheet and a leakage-preventing sheet.

The disposable diaper has its outer-face back sheet made of a nonwoven fabric prepared by an air-through method, in which fibers are thermally melted to each other at the time of manufacturing the nonwoven fabric by feeding hot air in a drum transfer process. This nonwoven fabric is arranged to have the aforementioned drum contacting face side on the inner face side of the diaper and the drum noncontact face side on the outer face side of the diaper, or the outer face side of the aforementioned outer-face back sheet is subjected to a raising treatment over a predetermined rangeset as at least the engaging range of the aforementioned fastening tapes. As a result, the engaging force of the fastening tapes can be improved, and at least the aforementioned front-side end flap portion $EF_F$ can be longitudinally folded back at an arbitrary position.

2 Claims, 10 Drawing Sheets

U.S. PATENT DOCUMENTS

| | | | |
|---|---|---|---|
| 4,681,581 A * | 7/1987 | Coates | 604/391 |
| 5,112,326 A * | 5/1992 | Quadrini | 604/385.3 |
| 5,295,986 A | 3/1994 | Zehner et al. | |
| 5,366,453 A | 11/1994 | Zehner et al. | |
| 5,601,547 A * | 2/1997 | Kato et al. | 604/385.3 |
| 5,690,627 A * | 11/1997 | Clear et al. | 604/385.29 |
| 5,722,969 A | 3/1998 | Ito et al. | |
| 5,836,930 A * | 11/1998 | Lantz et al. | 604/378 |
| 5,989,236 A | 11/1999 | Roe et al. | |
| 6,045,543 A * | 4/2000 | Pozniak et al. | 604/385.01 |
| 6,083,212 A * | 7/2000 | Kumasaka | 604/385.29 |
| 6,306,122 B1 * | 10/2001 | Narawa et al. | 604/385.3 |

FOREIGN PATENT DOCUMENTS

| | | |
|---|---|---|
| JP | 7-080024 | 3/1995 |
| JP | 7-308343 | 11/1995 |
| JP | 7-313552 | 12/1995 |
| JP | 7-328069 | 12/1995 |
| JP | 11-253209 | 9/1999 |
| JP | 2000-513639 | 10/2000 |
| JP | 2001-087309 | 4/2001 |
| JP | 2002-253608 | 9/2002 |
| JP | 2003-153952 | 5/2003 |
| JP | 2003-180748 | 7/2003 |

* cited by examiner

DISPOSABLE DIAPER HAVING FOLDED FRONT-SIDED END FLAP PORTION

BACKGROUND OF THE INVENTION

The present invention relates to a tape type disposable diaper, which has no front target tape on the outer face of the front of the diaper and which can adjust its size slightly.

In the prior art, the commercially available tape type paper diaper is provided with diaper wearing fastening tapes 50 and 50 on the two sides of the back of the paper diaper, for example, as shown in FIG. 16. When the paper diaper is used, its front and back are individually applied to the body of the wearer. After this, the aforementioned fastening tapes 50 and 50 are brought to the abdomen side, and are fastened to a front target tape 51 (as will be called the FTT), which is made of a plastic material such as polyethylene, a nonwoven fabric or a tricot and fixed by an adhesive agent to the surface of a liquid-impermeable sheet such as a polyethylene sheet of the outer face of the paper diaper (as referred to the following Patent Documents 1 and 2, for example).

It is hard to wear the paper diaper of this tape type snugly by a single fastening operation. As a matter of fact, it frequently occurs that the diaper is worn by several fastening operations. After one fastening tape 50 was fastened to the FTT 51, the other fastening tape 50 may fail to reach the FTT. In this case, it is troublesome to renew the fastening operation, and these several renewing operations may break the FTT.

In order to cope with these problems, there have been various disposable diapers, in which the aforementioned fastening tapes 50 are made not into the adhesion type but into a mechanical engagement type using hooks or the like, in which the back sheet constituting the outer face of the diaper is made of a nonwoven fabric, so that the aforementioned fastening tapes 50 are brought, when the diaper is worn, into direct engagement with the surface of the aforementioned outer-face back sheet (or a nonwoven fabric).

In the following Patent Document 3, for example, there is disclosed a disposable diaper comprising: a liquid-permeable surface sheet, a liquid-impermeable back sheet; an absorbing member interposed between those two sheets; fastening tapes for fixing the diaper when the diaper is worn; and release tapes for folding back the aforementioned fastening tapes, when unneeded, with folding-back portions to adhere their adhesive faces, wherein the aforementioned back sheet has a load of 100 g/cm to 300 g/cm at the extension of 3% of the aforementioned disposable diaper in the widthwise direction, a bulk softness of 55 g or less and a breakage strength of 250 g/cm or more; wherein the aforementioned fastening tapes have a 180-degree peeling force (i.e., a peeling force after lapse of 24 hours of RH at 40° C. and 80% after the adhesion to the aforementioned back sheet) of 400 g/cm or less and a holding time of 10 minutes or longer under a load of 500 g; and wherein the aforementioned back sheet has no reinforcing film for adhering the aforementioned fastening tapes.

In the following Patent Document 4, on the other hand, there is disclosed a paper diaper comprising an outer-face sheet having fastening members attached to the two back-side end portions of the paper diaper and hook elements on the fastening faces of the fastening members and forming the back of the aforementioned paper diaper which is made of a nonwoven fabric, wherein the hook elements of the aforementioned fastening members can engage, when the paper diaper is worn, with arbitrary portions of the surface of the aforementioned nonwoven fabric outer-face sheet. In the paper diaper, a target print for guiding the positions, at which the hook elements of the aforementioned fastening members are fastened, is so applied to at least one of the aforementioned nonwoven fabric outer-face sheet and the lower-side sheet as can be viewed from the outside.

In the following Patent Document 5, moreover, there is provided a disposable paper diaper of an FTT-less type, which is constituted such that the front and the back are formed by folding a diaper body including a liquid-permeable top sheet for covering the surface side, a liquid-impermeable back sheet for covering the back side, an absorbing member interposed between the aforementioned individual sheets, and diaper fastening tapes fixed on the two sides of the outer-side back portion of the aforementioned back sheet. In the disposable paper diaper, band-shaped sheets having a target print indicating the fastening positions of the fastening tapes are so disposed at the abdomen position of the aforementioned front that the print can be viewed from the outside.

Patent Document 1: JP-A-7-328069
Patent Document 2: JP-A-7-313552
Patent Document 3: JP-A-7-308343
Patent Document 4: JP-A-2002-253608
Patent Document 5: JP-A-2003-153952

In case, however, the mechanical type fastening tapes are brought into direct engagement with the nonwoven fabric forming the outer-face back sheet, as in the disposable diapers disclosed in the aforementioned Patent Documents 1 to 5, the engaging force between the mechanical type fastening tapes and the outer-face back sheet cannot be sufficiently retained, and the mechanical type fastening tapes may come out, while the diaper being worn, from the outer-face back sheet.

Moreover, the outer-face back sheet and the leakage-preventing sheet, as arranged on the inner-face side of the back sheet, are pattern-adhered by a hot-melt adhesive. When the aforementioned mechanical type fastening tapes are re-attached several times, there arises a problem that the aforementioned outer-face back sheet peels off the leakage-preventing sheet. Against this problem, the aforementioned Patent Document 2 subjects the fastened range to a dot-shaped embossing treatment thereby to prevent the outer-face back sheet from peeling off the leakage-preventing sheet. However, the embossing treatment makes the sheet hard thereby to cause a problem that the wearing feel is deteriorated. Moreover, a homogeneous application of the hot-melt adhesive and an increase in the quantity of application could also prevent the outer-face back sheet and the leakage-preventing sheet from peeling off. In this case, too, there arises a problem that the adhesive makes the sheet hard to deteriorate the wearing feel.

Moreover, a plurality of kinds of the tape type paper diaper of sizes for infants to LL are prepared according to the ages (or body sizes) of babies. In case, however, the body size of a baby is located intermediate of the sizes prepared, the paper diaper may fail to fit the body size thereby to establish a clearance from the body.

Therefore, a major object of the invention is to provide a disposable diaper, in which mechanical joining type fastening tapes are disposed on the two side portions of the back of the diaper and are brought, when the diaper is worn, into direct engagement with the surface of an outer-face back sheet (or a nonwoven fabric) made of the nonwoven fabric, so that the force of the fastening tapes to engage with the outer-face back sheet is improved without being accompanied by a drastic design change in the aforementioned outer-face back sheet and the fastening tapes.

SUMMARY OF THE INVENTION

In order to solve the aforementioned problem, according to a first aspect of the invention, there is provided a disposable diaper comprising: an absorbing member; a liquid-permeable top sheet covering the surface side of the absorbing member; a leakage-preventing sheet covering the backside of the absorbing member; an outer-face back sheet made of a nonwoven fabric and disposed on the outer face side of the leakage-preventing sheet; and mechanical joining type fastening tapes disposed on the two side portions of the back side of the diaper, wherein the fastening tapes are brought, when the diaper is worn, into direct engagement with the surface of said outer-face back sheet, wherein the outer-face back sheet is made of a nonwoven fabric manufactured by an air-through method, in which hot air is fed in a drum transfer process at a nonwoven fabric manufacturing time thereby to melt the fibers thermally to each other, and has its aforementioned drum contacting face side arranged on the diaper inner side and its drum non-contacting side arranged on the diameter outer side.

In the first aspect of the invention, the outer-face back sheet to be used is made of the nonwoven fabric manufactured by the air-through method, in which the hot air is fed in the drum transfer process at the nonwoven fabric manufacturing time thereby to melt the fibers thermally to each other, and has its aforementioned drum contacting face side arranged on the diaper inner side and its drum non-contacting side arranged on the diameter outer side. The air-through nonwoven fabric having the fibers melted to each other by the heat of the hot air is so totally high at a space ratio on the drum non-contacting face side as to give a plumy and bulky feeling while leaving relatively flat faces on the drum contacting sides. As a result, the hook portions of the fastening tapes can snugly engage to improve the engaging force of the fastening tapes with the outer-face back sheet. On the back-face side, on the other hand, the adhering efficiency is improved to improve the joining force between the outer-face back sheet and the leakage-preventing sheet.

In a second aspect of the invention, there is provided a disposable diaper comprising: an absorbing member; a liquid-permeable top sheet covering the surface side of the absorbing member; a leakage-preventing sheet covering the backside of the absorbing member; an outer-face back sheet made of a nonwoven fabric and disposed on the outer face side of the leakage-preventing sheet; and mechanical joining type fastening tapes disposed on the two side portions of the back side of the diaper, wherein the fastening tapes are brought, when the diaper is worn, into direct engagement with the surface of the outer-face back sheet, and wherein the outer-face back sheet is subjected on its outer face side to a raising treatment and a fiber peel preventing treatment within only a predetermined range set as the engaging range of the fastening tapes.

In the second aspect of the invention, the aforementioned outer-face back sheet is subjected to the raising treatment within only a predetermined range set as the engaging range of at least the fastening tapes. As a result, the engaging force of the aforementioned fastening tapes can be drastically improved without being accompanied by large-scale design changes of the aforementioned outer-face back sheet and the fastening tapes. Moreover, the outer-face back sheet is subjected to the fiber peel preventing treatment thereby to prevent the fibers from being easily peeled off by the aforementioned raising treatment.

In a third aspect of the invention, there is provided a disposable diaper according to the second aspect of the invention, wherein the fiber peel preventing treatment is a roller compressing treatment of the raised face.

In a fourth aspect of the invention, there is provided a disposable diaper according to the second aspect of the invention, wherein the fiber peel preventing treatment is an adhesive applying treatment.

In a fifth aspect of the invention, there is provided a disposable diaper of any of the second to fourth aspects of the invention, wherein an air-through nonwoven fabric or a spun-bonded nonwoven fabric is used as the outer-face back sheet. The air-through nonwoven fabric or the spun-bonded nonwoven fabric having its fibers thermally melted to each other is used as the outer-face back sheet so that the fibers can be prevented from coming out thereby to retain the stable engaging force.

In a sixth aspect of the invention, there is provided a disposable diaper of any of the first to fifth aspects of the invention, further comprising a front-side end flap portion and a back-side end flap portion having no absorbing member, respectively, at the front and back end portions in the longitudinal direction of the diaper; wherein at least the front-side end flap portion is formed over at least a length range of 5% or more of the diaper product in the longitudinal direction from the diaper end edge; wherein the front-side end flap portion has no elastically extendible member arranged, but the aforementioned leakage-preventing sheet extends slightly to the outer-side from the front-side end edge of the absorbing member and is joined to the aforementioned liquid permeable top sheet; and wherein the aforementioned front-side end flap is substantially composed of a liquid-permeable top sheet and the outer-face back sheet so that the front-side end flap portion can be longitudinally folded at an arbitrary position.

According to the aforementioned sixth aspect of the invention, there is provided a disposable diaper, which is enabled to adjust its size slightly according to the body shape of a baby. In the invention, the front-side end flap portion is formed over at least a length range of 5% or more of the diaper product in the longitudinal direction from the waist opening edge, and the front-side end flap portion has no elastically extendible member arranged. The size adjustment is performed by holding back the front-side end flap portion, which is desired to be slightly longer than that of the ordinary diaper. The aforementioned front-side end flap portion is substantially constituted of the liquid-permeable top sheet and the outer-face back sheet. Because of the absence of the leakage-preventing sheet, the flexibility (or softness) is improved to facilitate the folding-back so that the wearability is not deteriorated even in the folded-back case.

In a seventh aspect of the invention, there is provided a disposable diaper comprising: an absorbing member; a liquid-permeable top sheet covering the surface side of the absorbing member; a leakage-preventing sheet covering the backside of the absorbing member; an outer-face back sheet made of a nonwoven fabric and disposed on the outer face side of the leakage-preventing sheet; and mechanical joining type fastening tapes disposed on the two side portions of the back side of the diaper, wherein the fastening tapes are brought, when the diaper is worn, into direct engagement with the surface of the outer-face back sheet, and further comprising a front-side end flap portion and a back-side end flap portion having no absorbing member, respectively, at the front and back end portions in the longitudinal direction of the diaper; wherein at least the front-side end flap portion is formed over at least a length range of 5% or more of the diaper product in the longitudinal direction from the diaper end edge; and wherein the front-side end flap portion has no elastically extendible member arranged, but the aforementioned leakage-preventing sheet extends slightly to the outer-side from the front-side end edge of the absorbing member and is joined to the aforementioned liquid permeable top sheet; and wherein the aforementioned front-side end flap is substantially composed of a liquid-permeable top sheet and the outer-face back sheet so that the front-side end flap portion can be longitudinally folded at an arbitrary position.

In the aforementioned sixth and seventh aspects of the invention, there is provided a disposable diaper, in which the front outer face does not have any front target tape, and the aforementioned fastening tapes are made to engage directly with the surface of the aforementioned outer-face back sheet. Because of the absence of the front target tape, no trouble arises when the front-side end flap portion is folded back at an arbitrary position.

Moreover, at least the front-side end flap portion is formed over at least a length range of 5% or more of the diaper product in the longitudinal direction from the diaper end edge (or the waist opening edge). As a result, the size adjustment can be made to cover the intermediate range of the diaper size. Here, the length of forming the aforementioned front end flap portion is at least 10 mm or more in the longitudinal direction from the diaper end edge, preferably 20 mm or more, or more preferably 30 mm or more.

Moreover, the front-side end flap portion has no elastically extendible member arranged so that it can be easily folded because of absence of a member to obstruct the folding-back.

In an eighth aspect of the invention, there is provided a disposable diaper of the sixth or seventh aspect of the invention, wherein the front-side end flap portion is provided on its outer-face side with a folding position guide indication visibly from the outside.

In the aforementioned eighth aspect of the invention, the front-side end flap portion is provided on its outer-face side with the folding position guide indication visibly from the outside. At the wearing time, the folding-back position can be determined resorting to the guide indication of that folding position. It is, therefore, possible to adjust the diaper always to the desired constant size.

In a ninth aspect of the invention, there is provided a disposable diaper of the sixth or seventh aspect of the invention, wherein the front-side end flap portion is provided with a plurality of linear or band-shaped portions having a degree of rigidity different from that of the front-side end flap portion, at an interval longitudinally of the diaper and along the widthwise direction of the diaper. In the ninth aspect of the invention, the provision of the aforementioned linear or band-shaped portions can facilitate the folding-back operation of the front-side end flap portion.

In the tenth aspect of the invention, there is provided a disposable diaper of any of the sixth to seventh aspects of the invention, wherein the length of forming the front-side end flap portion from the diaper end edge is set larger than that of forming the back-side end flap portion from the diaper end edge.

In the tenth aspect of the invention, the length of forming the front-side end flap portion from the diaper end edge is made larger than that of forming the back-side end flap portion from the diaper end edge. Generally, the lengths of the front end flap portion and the back end flap portion are made substantially equal. In the present disposable diaper, however, it is desired that the front end flap portion is made longer than the back end flap portion because it is a size adjusting allowance.

According to the invention, as has been detailed hereinbefore, the force of the fastening tapes to engage with the outer-face back sheet can be improved without being accompanied by a drastic design changes in the outer-face back sheet and the fastening tapes. Moreover, the slight size adjustment can be made according to the body size of a baby.

BEST MODE FOR CARRYING OUT THE INVENTION

Modes of embodiment of the invention are described in detail in the following with reference to the accompanying drawings.

BRIEF DESCRIPTION OF THE DRAWINGS

In FIG. 1, a disposable diaper 1 is composed mainly of: an absorbing member 4 made of flaky pulp or the like into a hourglass shape (or a rectangular shape) having a rigidity and enclosed by a crepe paper 5; a liquid-permeable top sheet 3 made of a porous or nonporous nonwoven fabric or a pored plastic sheet and arranged to cover the surface side (or the used side) of the absorbing member 4; a leakage-preventing sheet 6 made of polyethylene or the like and so arranged on the back side of the aforementioned absorbing member as to cover at least the entire area of the absorbing member 4; an outer-face back sheet 2 made of a nonwoven fabric and so disposed on the outer-face side (or a skin unabutting side) of that leakage-preventing sheet 6 as to define the diaper contour; side non-woven fabrics 7 and 7 for forming three-dimensional gathers BS rising from the two side portions of the paper diaper to the surface side and for constituting side flap portions SF on the two side portions of the diaper together with the aforementioned leakage-preventing sheet 6 and the back sheet 2; and mechanical joining type fastening tapes 10 and 10 disposed on the two side portions of the diaper back. At the abdomen waist portion and the back-side waist portion of the paper diaper, moreover, there are formed end flap portions EF, in which the aforementioned outer-face back sheet 2, the leakage-preventing sheet 6 and the liquid-permeable top sheet 3 exist altogether but in which the absorbing member 4 does not exist.

Figure 3:
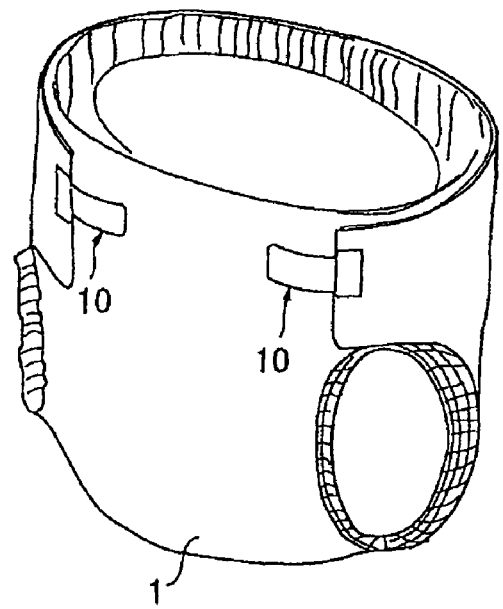
FIG. 3 A view showing the worn state of the disposable diaper 1.

When the paper diaper is worn, as shown in FIG. 3, the front and back of the paper diaper 1 are applied to the body of the wearer, and the aforementioned fastening tapes 10 and 10 are brought to the abdomen side into direct engagement with the surface of the outer-face back sheet 2.

The individual components are more specifically described in the following.

The aforementioned absorbing member 4 is made of fluffy pulp and water-absorbing polymer, for example, and is formed generally into an hourglass shape having two thinned side portions in the shown example to soften the abutments against the legs. The aforementioned water-absorbing polymer is mixed as granular powder, for example, into the pulp composing the absorber. The aforementioned pulp is exemplified by cellulose fibers such as chemical pulp or dissolving pulp made of wood, or artificial cellulose fibers such as rayon or acetate. Soft wood pulp having larger fiber lengths is better employed than hard wood pulp because of its function and price. In case the absorbing member 4 is enclosed by the crepe paper 5, as shown in the drawing, the crepe paper resultantly exists between the liquid-permeable surface sheet 3 and the absorbing member 4, so that the bodily liquid can be promptly diffused by the aforementioned crepe paper 5 excellent in the absorptivity thereby to prevent the backflow of menstrual blood or the like.

The aforementioned liquid-permeable top sheet 3 is better exemplified by porous or nonporous nonwoven fabric or a porous plastic sheet. The material fiber forming the nonwoven fabric can be exemplified not only synthetic fibers such as an olefin group, e.g., polyethylene or polypropylene, a polyester group, or a polyamide group but also reproduced fibers such as rayon or cupra, or natural fibers such as cotton. The material fiber can be exemplified by nonwoven fabric prepared by a suitable working method such as a spun-lacing method, a spun-bonding method, a thermal bonding method, an air-through method, a melt-blown method or a needle punching method. Of these working methods, the spun-lacing method is excellent in softness and in richness of a draping property, and the thermal bonding method is excellent in bulkiness and softness.

The aforementioned leakage-preventing sheet 6 is made of a sheet material having at least water-repelling property such as a resin sheet of the olefin group such as polyethylene or polypropylene, and is disposed within a range to cover at least the entire area of the absorbing member 4 so as to prevent the leakage. In recent years, the sheet material having a moisture permeability is preferably used with a view to preventing the stuffiness. This water-repelling/moisture-permeable sheet is exemplified by a finely porous sheet, which is obtained by solving and kneading an inorganic filler into an olefin resin such as polyethylene or polypropylene to form a sheet and then by blending the same in one or two axial directions. The finely porous sheet is superior in softness to a nonporous sheet, if the sheets have an equal thickness, because its rigidity drops.

From the point of emphasis, the aforementioned side nonwoven fabrics 7 can be exemplified by a water-proofed nonwoven fabric or a hydrophilic nonwoven fabric. If the function to prevent the menstrual blood or vaginal discharge from penetrating or to enhance the skin touch is emphasized, for example, it is desired to use the water-repelling nonwoven fabric, which is coated with a water repelling agent of silicon group, paraffin group or alkyl chromic chloride. If the absorptivity of the bodily liquid or the like is emphasized, on the other hand, it is desired to use a hydrophilic nonwoven fabric. When this hydrophilic nonwoven fabric is prepared, synthetic fibers are desirably swelled or made porous by either a method to polymerize the synthetic fibers in the presence of a compound having hydrophilic groups such as an oxide product of polyethylene glycol or a method to treat the surface with a metallic salt such as stannic chloride to dissolve the surface partially and to make the same porous thereby to deposit the hydroxide of the metal. Thus, the hydrophilic nonwoven fabric is given the hydrophilic property by applying the capillary phenomenon.

The aforementioned liquid-permeable top sheet 3 is protruded-slightly outward from the side edges of the absorbing member 4 so that it is joined to the aforementioned leakage-preventing sheet 6. The aforementioned side non-woven fabrics 7 are extended more at their outer-side portions than the vicinities of the side edge portions of the aforementioned absorbing member 4, and are joined to the aforementioned leakage-preventing sheet 6 and the outer-face back sheet 2 so that their laminated sheet portions constitute the side flap portions SF.

In these side flap portions SF, a plurality of elastically extendible members 8 and 8 or two in the shown embodiment are arranged in the longitudinal direction of the paper diaper 1 thereby to form plane gathers. These plane gathers hold the paper diaper, when worn, snugly around the legs so that they improve the fitness to prevent the paper diaper from going out of position.

On the other hand, the nonwoven fabric sheet portions of the aforementioned side non-woven fabrics 7 on the inner sides of the joined portions form the three-dimensional gathers BS rising on the surface side. These three-dimensional gathers BS have their rising ends at positions near the side edges of the absorbing member 4, and have their leading ends doubly folded back along the longitudinal direction of the paper diaper. Inside of these folded portions, one elastically extendible member 9 or, if necessary, a plurality of elastically extendible members are arranged to make use of their stretching forces thereby to raise the three-dimensional gathers BS.

The aforementioned elastically extendible members 8 and 9 can be exemplified by ordinarily used members such as styrene group rubber, olefin group rubber, urethane group rubber, ester group rubber, polyurethane, polyethylene, polystyrene, styrene butadiene, silicone or polyester.

The material fibers to compose the aforementioned side non-woven fabrics 7 can be exemplified by not only synthetic fibers of an olefin group such as polyethylene or polypropylene, a polyester group or a polyamide group, but also reproduced fibers such as rayon or cupra, or natural fibers such as cotton. The material fibers can be exemplified by the nonwoven fabric, which is prepared by a suitable working method such as the spun-bonding method, the air-through method, the melt-blown method or the needle punching method. However, especially the aforementioned side nonwoven fabrics 7 forming the side flap portions SF may be exemplified by the nonwoven fabric, which is excellent in air-permeability while suppressing the aerial weight, so as to eliminate the stiffness and prevent the stuffiness.

The aforementioned mechanical joining type fastening tapes 10 are joined at the root portions of fastening base members 10A of plastics, a poly-laminated nonwoven fabric, a nonwoven fabric or paper to the diaper. The fastening tapes 10 are provided with hook elements 10B at the protruding member portions and on the surface sides (i.e., the faces of the side of the liquid-permeable top sheet 3) of the aforementioned fastening base members 10A. The aforementioned hook elements 10B are so adhered to the fastening base members 10A by means of an adhesive that they can not peel off. The aforementioned hook elements 10B are provided with a number of engaging members 10b,10b and so on on their outer faces. These engaging members 10b may have any of shapes including a V-letter shape, a J-letter shape, a mushroom shape and a T-letter shape. Of these, the mushroom shape or the T-letter shape is preferred. In the product state, the aforementioned fastening tapes 10 are so folded to the sides of the liquid-permeable top sheet 3 that the aforementioned hook elements 10B are peelably joined to the side non-woven fabrics 7.

Moreover, it is preferred that the ratio of arrangement of the aforementioned engaging members 10b is 900 to 1,600 pieces/inch². This is because the ratio of 900 pieces/inch² or less is not sufficient for the force to engage with the outer-face back sheet 2 and because the ratio of 1,600 pieces/inch²or more may break the outer-face back sheet 2 when the fastening tapes 10 are attached/detached. Moreover, it is preferred that the aforementioned engaging members 10b have a head diameter of 330 to 550 μm. As a result, it is possible to keep the engaging force of the fastening tapes 10 and to prevent the breakage of the outer-face back sheet 2.

On the other hand, the aforementioned outer-face back sheet 2 made of the nonwoven fabric is exemplified by the nonwoven fabrics of various kinds, which have been subjected on their outer face sides to a raising treatment by the means, as will be described in the following.

Figure 4:
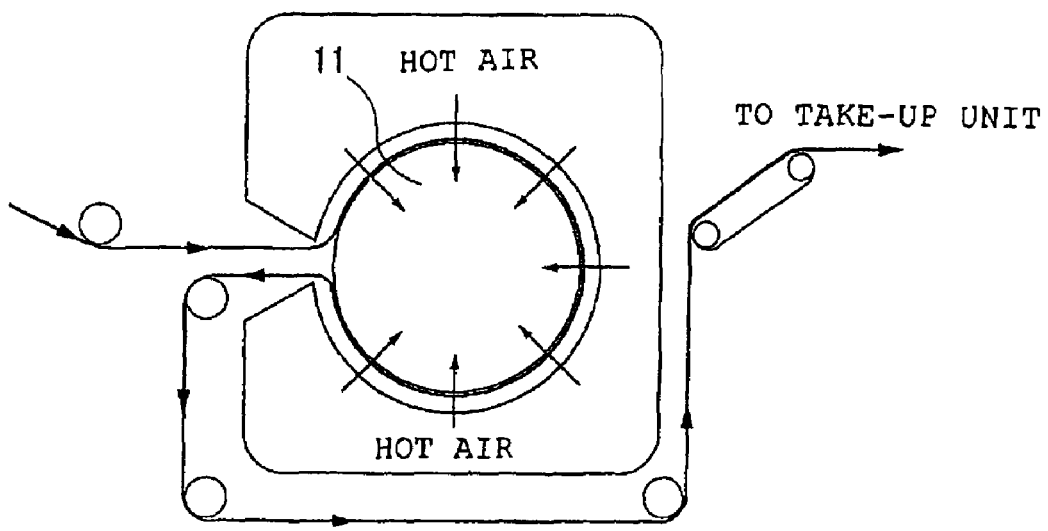
FIG. 4 An explanatory diagram of an air-through method.
Figure 5:
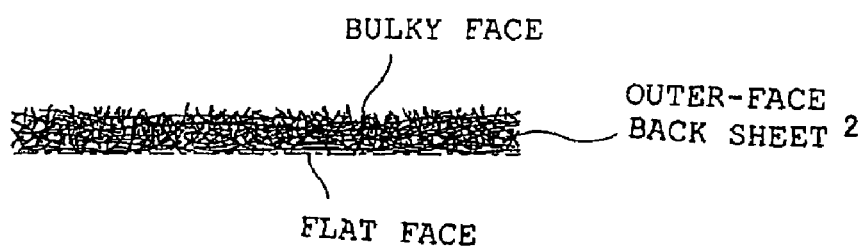
FIG. 5 An enlarged section of an outer-face back sheet 2.
Figure 6:
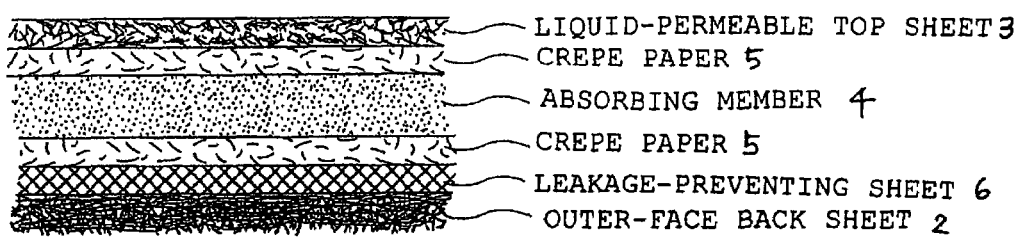
FIG. 6 An enlarged section showing the layer constitution of the diaper.

The first raising means is the air-through method, in which heated air is fed in a drum transfer process at the time of manufacturing the nonwoven fabric thereby to melt the fibers thermally to each other. The aforementioned air-through method is one of the nonwoven fabric manufacturing methods, in which hot air is applied from the outside at the fiber adhering step, after the nonwoven web was formed by the well-known method such as a dry or wet method of an air lay method or a card method, in the process of turning and transferring a drum 11, as shown in FIG. 4, thereby to melt the fibers to each other. The resulting nonwoven fabric is advantageous in that the space ratio is so high as to give fluffy touch and it is bulky because the fibers are melted by the heat of the hot-air without undergoing calendering treatment unlike the thermal bonding method. In the cross-sectional view, as shown in FIG. 5, the drum non-contacting side of the nonwoven fabric is a bulky face giving a fluffy touch with a high inner space ratio and having a bulkiness, while the drum contacting side is a relatively flat face.

As a result, the aforementioned outer-face back sheet 2 has its aforementioned drum contacting face side arranged on the diaper inner side and its drum non-contacting side arranged on the diameter outer side, so that the engaging members 10b of the aforementioned fastening tapes 10 come into firm contact with the bulky face of the outer-face back sheet 2 thereby to improve the engaging forces. Moreover, the contact faces with the leakage-preventing sheet 6 is made so flat that the hot-melt adhesive applied does not fill the spaces between the fibers but contacts the leakage-preventing sheet 6 over a wide area so that the adhering strength of the hot-melt adhesive is improved. The force of the aforementioned fastening tapes 10 to engage with the outer-face back sheet 2 is desired to be 10 g or higher in terms of the shearing force and 2.5 g or higher in terms of a tensile force (or a peeling force). The nonwoven fabric forming the aforementioned outer-face back sheet 2 is desired to have a denier number of 1.0 to 15d and a basis weight of 15 to 30 g/m².

In the manufacture of the nonwoven fabric by the air-through method according to the aforementioned first raising means, experiments were performed to determine the optimum working conditions. On the nonwoven fabrics manufactured by a nipping treatment by varying the air temperature and the calender temperature, specifically, the peeling strengths between the formed layers and the engaging forces of the fastening tapes 10 were measured and evaluated. As a result, emphasizing the inter-layer peeling strengths of the nonwoven fabric, as tabulated in Table 1,it is preferred that the aforementioned outer-face back sheet 2 is manufactured by the air-through method under the conditions of the air temperature of 130.5 to 135° C. and the calender temperature of 124° C.±2° C. Emphasizing the engaging force of the fastening tapes 10, on the other hand, it is preferred that the outer-face back sheet 2 is manufactured by the air-through method under the conditions of the air temperature of 130.5 to 132.5° C. and the calender temperature of 115 to 124° C. In order to balance those conditions well, it is preferred that the aforementioned outer-face back sheet 2 is manufactured by the air-through method under the conditions of the air temperature of 131.5° C.±1° C. and the calender temperature 124° C.±2° C. Here in Table 1,evaluations were made such that Circle: Strong, Triangular: Rather Strong, and X: Weak.

TABLE 1

|  | Air Temp. ° C. | Calender Temp. ° C. | Working Method | Inter-Layer Peel | Eng. Force |
| --- | --- | --- | --- | --- | --- |
| Ex. 1 | 130.5 | 115 | Nipping | x | ○ |
| Ex. 2 | 130.5 | 118 | Nipping | x | ○ |
| Ex. 3 | 130.5 | 121 | Nipping | x | ○ |
| Ex. 4 | 130.5 | 124 | Nipping | ○ | ○ |
| Ex. 5 | 132.5 | 124 | Nipping | ○ | Δ |
| Ex. 6 | 135.0 | 124 | Nipping | ○ | x |

Figure 7:
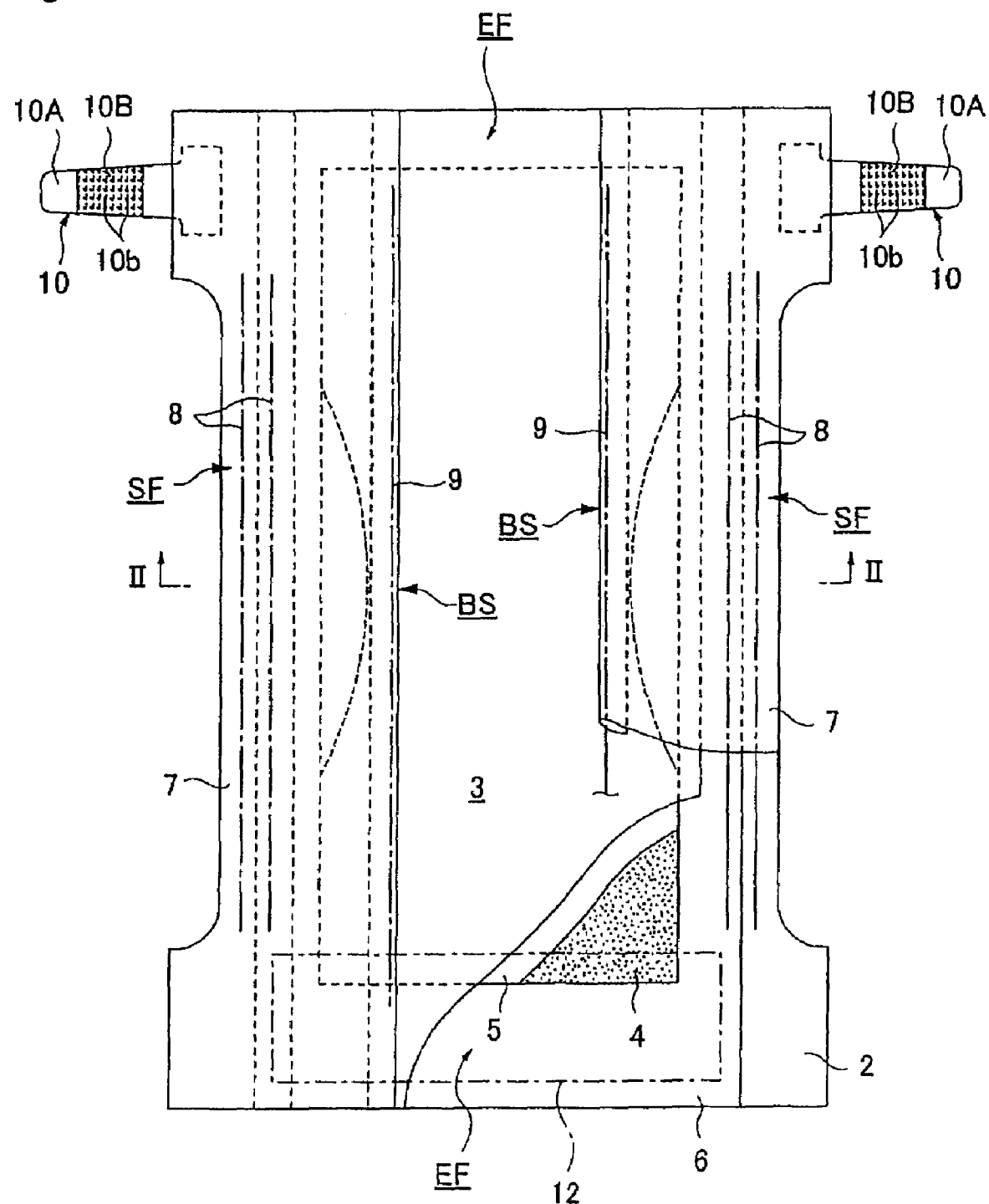
FIG. 7 A partially broken development of a disposable diaper 1 according to the invention, to which second raising means is applied.

Next, the second raising means passes the raising roll through a predetermined range 12 (as will be called the "raised range"), which is supposed as the engaging range of at least the aforementioned fastening tapes 10 on the outer face side, as shown in FIG. 7. The aforementioned raising range 12 can be arbitrarily set, but is desirably set sufficiently wide by considering the body difference.

The material fiber forming the nonwoven fabric can be exemplified not only synthetic fibers such as an olefin group, e.g., polyethylene or polypropylene, a polyester group, or a polyamide group but also reproduced fibers such as rayon or cupra, or natural fibers such as cotton. The material fiber can be exemplified by nonwoven fabric prepared by a suitable working method such as the spun-lacing method, the spun-bonding method, the thermal bonding method, the air-through method or the needle punching method. Of these nonwoven fabrics, however, it is desired to employ the air-through nonwoven fabric or the spun-bonded nonwoven fabric. These nonwoven fabrics have their fibers firmly thermally-melted to each other so that the drop-out of the fibers can be suppressed to retain a stable engaging force.

Figure 8:
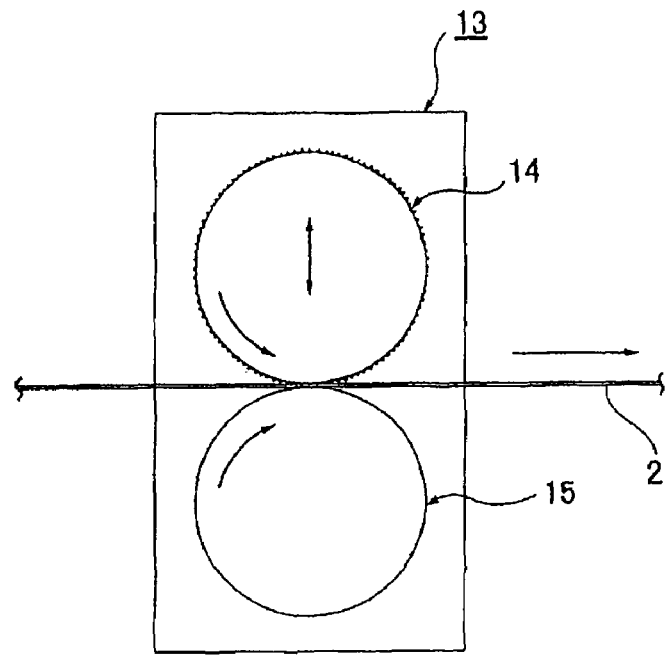
FIG. 8 A diagram showing the summary of a raising treatment.

The raising treatment of the nonwoven fabric forming the aforementioned outer-face back sheet 2 can be performed with a raising facility 13 having a raising roll 14 and an anvil roll 15 arranged to confront each other, by passing the nonwoven web (or the outer-face back sheet web) between those rolls 14 and 15, as shown in FIG. 8. The aforementioned raising roll 14 is provided on its surface with raising means for a sanding treatment or the like, which has a number of pins or needles embedded or a number of particles fixed thereon. The nonwoven fabric of the outer-face back sheet 2 is raised by bringing the raising means into contact with the outer-face back sheet 2 while turning the same at a faster speed than the line speed of the web (or the outer-face back sheet 2). Here in case the pins or needles are employed to raise the outer-face back sheet 2, they may have no hook or the like at their leading end portions.

Figure 9:
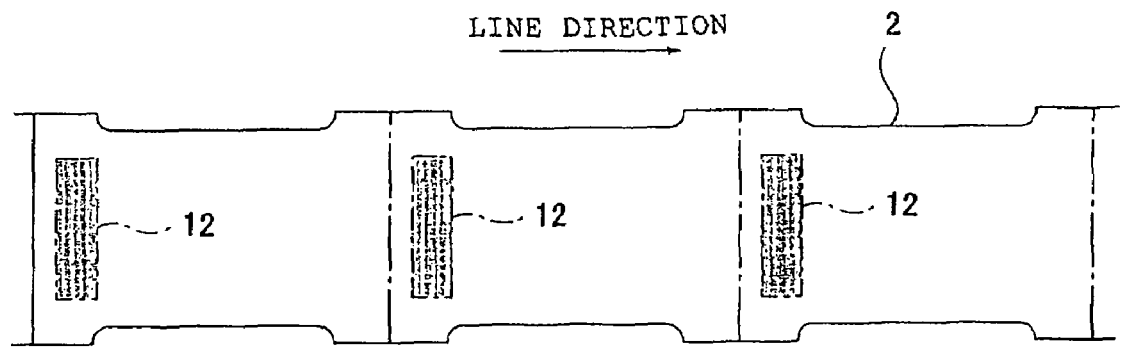
FIG. 9 A state diagram of forming a raised range 12 on the web (or the outer-face back sheet 2).

When the raised areas are to be formed at a predetermined interval on the web in accordance with the aforementioned raised range 12, as shown in FIG. 9, the aforementioned raising roll 14 may be controlled to slide up and down by a piston or the like and to rise and fall synchronously. Here, the rotations of the raising roll 14 may be in the same direction as or in the opposite direction to that of the web. However, the latter direction is higher in the raising effect. Moreover, the raising degree can be adjusted by adjusting the clearance (or nip) between the raising roll 14 and the anvil roll 15.

The force of the aforementioned fastening tapes 10 to engage with the outer-face back sheet 2 is desired to be 10 g or higher in terms of the shearing force and 2.5 g or higher in terms of the tensile force (or the peeling force). The nonwoven fabric forming the aforementioned outer-face back sheet 2 is desired to have the denier number of 1.0 to 15 $d$ and the basis weight of 15 to 30 g/m$^2$.

Here, as the force of the fastening tapes 10 to engage with the outer-face back sheet 2 is improved by the aforementioned raising treatment, there newly arises a problem that the fibers of the outer-face back sheet 2 become liable to come out. In order to prevent the fibers from coming out, therefore, it is desired to subject the raised face to the fiber peel preventing treatment by the roller compression and/or to the fiber peel preventing treatment by the adhesive application. Alternatively, it is possible to subject the back face side of the aforementioned raised face to the fiber peel preventing treatment by the adhesive application or to the fiber peel preventing treatment by the fiber melting treatment with a heat roll. In terms of safety, the hot melt adhesive is preferred in the aforementioned adhesives. Here, it is possible to perform together the fiber peel preventing treatment of the aforementioned raised face and the fiber peel preventing treatment of the back face of the raised face.

Figure 1:
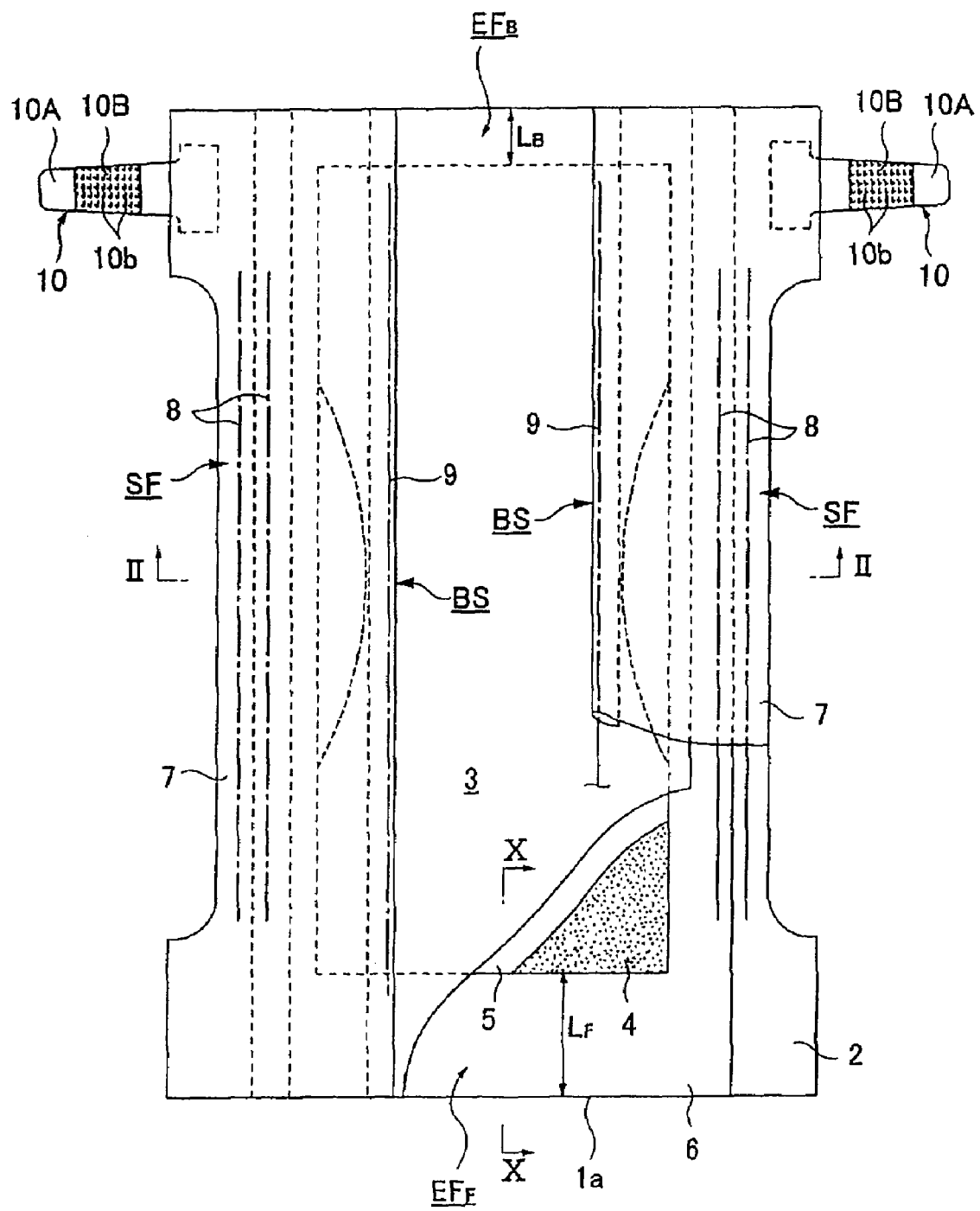
FIG. 1 A partially broken development of a disposable diaper 1 according to the invention.
Figure 2:
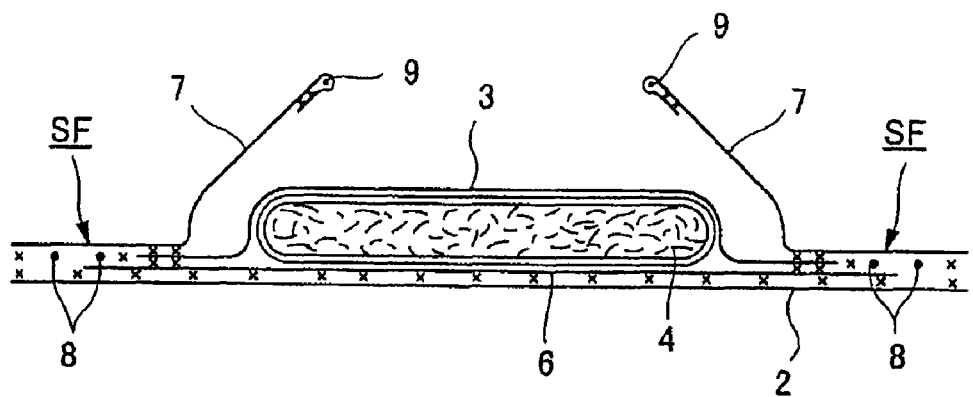
FIG. 2 A view taken along line II-II of FIG. 1.
Figure 10:
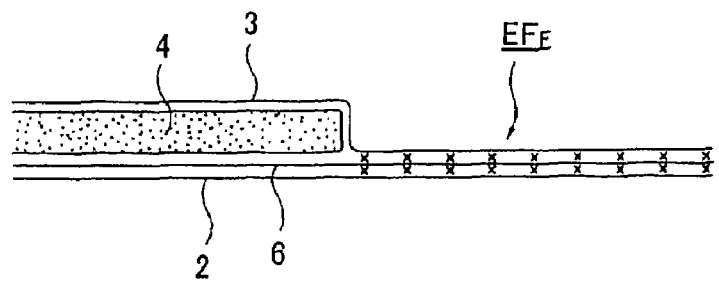
FIG. 10 A view taken along line III-III of FIG. 1.

Next, size adjusting means for the disposable diaper according to the invention is described in detail. At the front and back end portions of the aforementioned disposable diaper, as shown in FIG. 1 and FIG. 10, the aforementioned outer-face back sheet 2, leakage-preventing sheet 6 and liquid-permeable top sheet 3 individually extend altogether to form end flap portions $EF_B$ and $EF_F$, in which the absorbing member 4 is absent.

In the present disposable diaper 1, especially the aforementioned front end flap portion $EF_F$ is formed in the longitudinal direction from a waist opening edge 1$a$ over at least 5% or higher of the diaper product, preferably 10% or higher of a length range $L_F$, and the front end flap portion $EF_F$ has no elastically extendible member arranged so that it can be longitudinally folded back at an arbitrary position. Here, the length of forming the aforementioned front end flap portion $EF_F$ is desirably made, although different in dependence upon the diaper size, within a range of at least 10 mm or more from the diaper end edge 1$a$, preferably 20 mm or more and more preferably 30 mm or more.

By folding back the aforementioned front end flap portion EFF in the longitudinal direction at an arbitrary position, therefore, the size adjustment can be made in an extent to cover the intermediate range of the diaper size. In case the length of the aforementioned front-side end flap portion $EF_F$ is set less than 5% of the diaper product length, it is impossible to make the desired size adjustment. It is also desired to set the length $L_F$ of the aforementioned front-side end flap portion $EL_F$ from the waist opening edge 1$a$ larger than the length $L_B$ of the back end flap portion $EF_B$ from a waist opening edge 1$b$. In this case, the difference between the length $L_F$ of the front end flap portion $EF_F$ from the waist opening edge 1$a$ and the length $L_B$ of the back end flap portion $EF_B$ from the waist opening edge 1$b$ may be 5 mm or more, preferably 10 mm or more, and more preferably 15 mm or more.

Figure 11A:
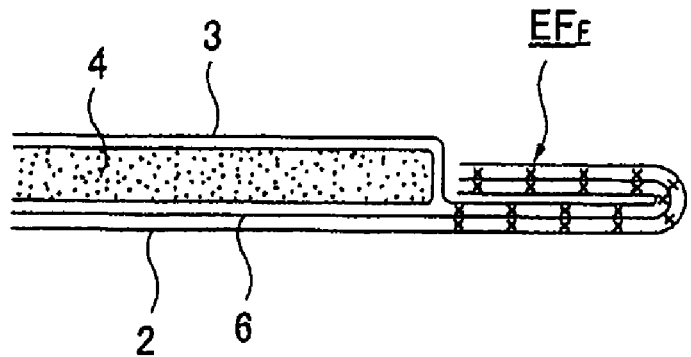
FIGS. 11(A) to 11(C) Diagrams showing the folded modes of a front-side end flap portion $EF_F$.
Figure 11B:
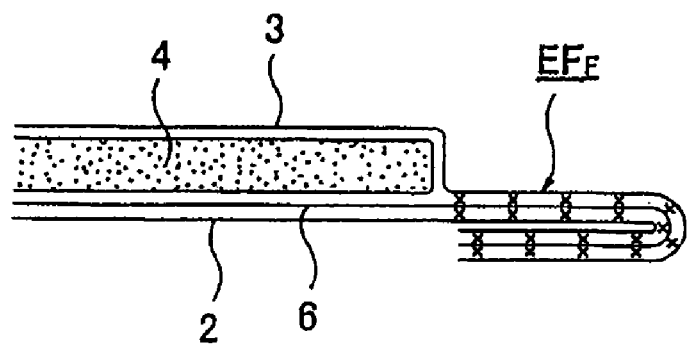
Figure 11C:
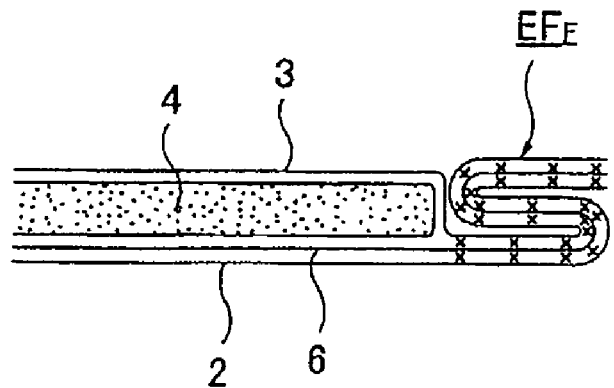

The folding-back modes of the front end flap portion $EF_F$ may be exemplified by folding it to the inner face side, as shown in FIG. 11(A), to the outer face side, as shown in FIG. 11(B), or to a Z-shaped section, as shown in FIG. 11(C). In the aforementioned case of folding back to the inner face side, as shown in FIG. 11(A), it is possible to dam up the urine or feces at the folded-back portion.

Here in the modes shown in FIG. 11(A) to 11(C), the front end flap portion EFF is longitudinally folded back at its intermediate portion. The folding-back may be so located at an arbitrary position as to fit the size of a baby within the range from the waist opening edge 1$a$ to the side edges of the absorbing member 4.

Figure 12:
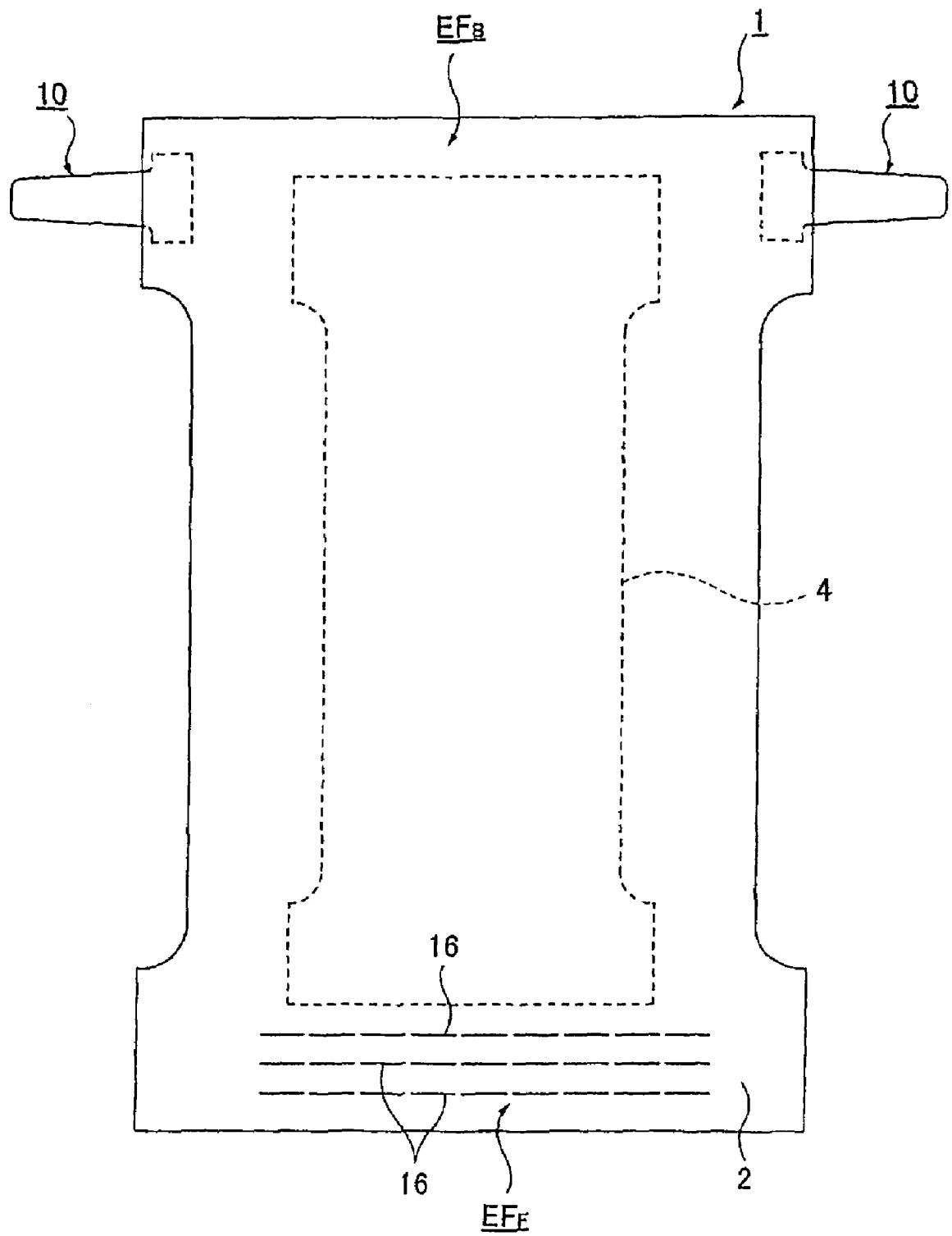
FIG. 12 A diaper back elevation of the case, in which folding position guide lines 16 are formed.

On the other hand, the aforementioned outer-face back sheet 2 is printed with one or more displays indicating the guides of the folding positions, that is, one or more, i.e., three folding position guide lines 16, 16 and so on, as shown in FIG. 12. Moreover, these folding position guide lines 16 can be formed in the outer-face back sheet 2 and/or the liquid-permeable top sheet 3. Here, these folding position guide lines 16 may be visible from the outside. Specifically, the guide lines 16 may be printed on the outer face side of the leakage-preventing sheet 6 so that they may be seen through the outer-face back sheet 2 and/or printed on the inner face side of the leakage-preventing sheet 6 so that they may be seen through the liquid-permeable top sheet 3. Alternatively, another sheet printed with the folding position guide lines 16 may be interposed between the leakage-preventing sheet 6 and the outer-face back sheet 2 and/or between the leakage-preventing sheet 6 and the liquid-permeable top sheet 3. Still alternatively, the individual lines may be differently colored.

Figure 13A:
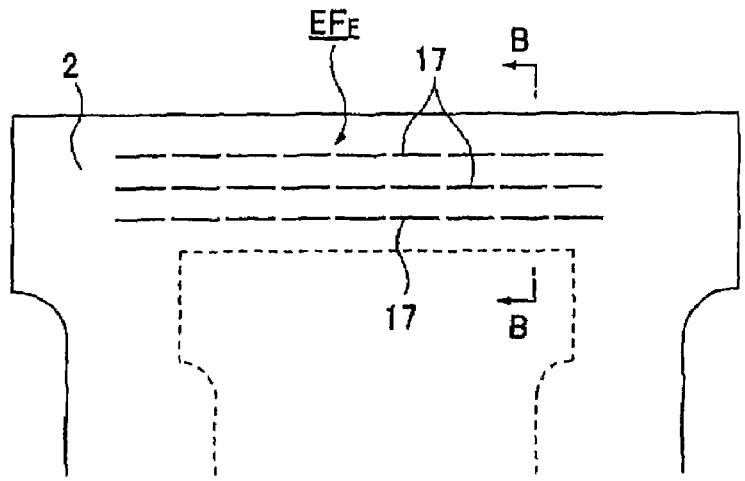
FIG. 13 (A) An enlarged diagram of the front-side end flap portion $EF_F$ of the case, in which linear or band-shaped portions 17 are formed, and (B) to (D) Sections B-B of (A) showing modes of embodiment of the linear or band-shaped portions 17.
Figure 13B:
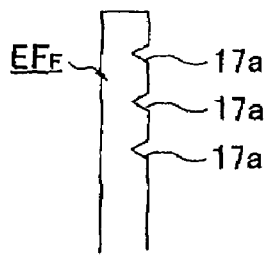
Figure 13C:
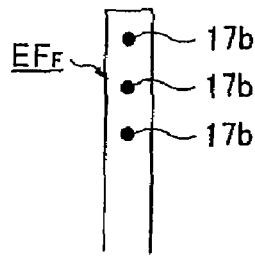
Figure 13D:
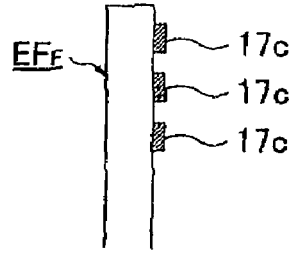

Moreover, the disposable diaper according to the invention can be provided with a plurality of linear or band-shaped portions 17, 17 and so on having a degree of rigidity different from that of the front-side end flap portion $EF_F$, in the front-side end flap portion $EF_F$ at an interval in the longitudinal direction of the diaper and along the widthwise direction of the diaper, as shown in FIG. 13(A), so as to facilitate the folding operations. As shown in FIG. 13(B) to 13(D), the aforementioned linear or band-shaped portions 17 can be formed by an embossing work to provide emboss lines (or grooves) 17$a$, by interposing rubber threads 17$b$ between the leakage-preventing sheet 6 and the outer-face back sheet 2 and/or between the leakage-preventing sheet 6 and the liquid-permeable top sheet 3, by disposing other members 17$c$ on the outer-face back sheet 2 or the liquid-permeable top sheet 3. At this time, it is desired that those linear or band-shaped portions 17 are horizontal straight lines in the diaper widthwise direction. The provision of the aforementioned linear or band-shaped portions 17 can facilitate the folding-back operations. These linear or band-shaped portions 17 are made into the straight lines horizontal in the diaper widthwise direction so that the folds can be the horizontal straight lines. As a result, the diaper can have no wrinkle, after folded back, to fit the body thereby to prevent the bodily liquid from oozing out and thereby to improve the design appearance of the diaper.

Other embodiments of the invention are as follows.

(1) In the aforementioned mode of embodiment, the outer-face back sheet 2 and the leakage-preventing sheet 6 are made separate but can also be exemplified by a laminated nonwoven fabric having a film and a nonwoven fabric laminated in advance.

Figure 14:
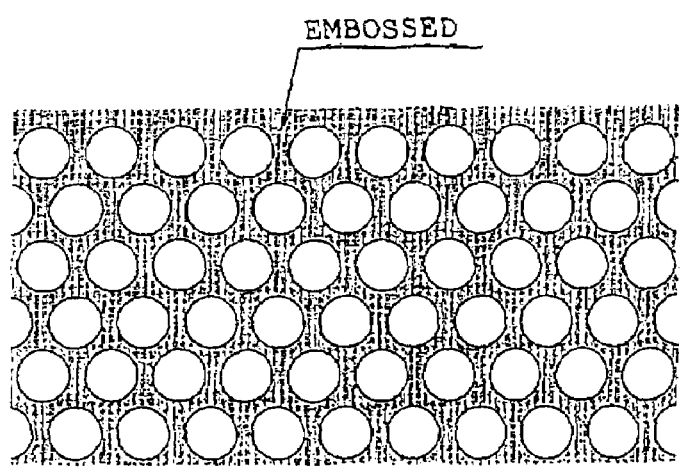
FIG. 14 A top plan view of an essential portion showing an embossed pattern of the outer-face back sheet 2.

(2) The aforementioned outer-face back sheet 2 can have its outer face embossed, as shown in FIG. 14, to give the soft feeling. Although various embossed patterns can be made, as shown in the same Figure, circles are left (unworked) in a staggered pattern, and the remaining area is embossed. It is desired that the unworked portion is formed into a shape having no corner, for example, into a circular or elliptical shape, and that the array is staggered or aligned. In case the embossed area is large, the engaging force of the fastening tapes 10 falls. It is, therefore, advisable that the embossed area is 30% or less. Moreover, the aforementioned embossed area either may occupy the entirety of the aforementioned outer-face back sheet 2 or may be limited to the joined areas of the fastening tapes 10.

Figure 15:
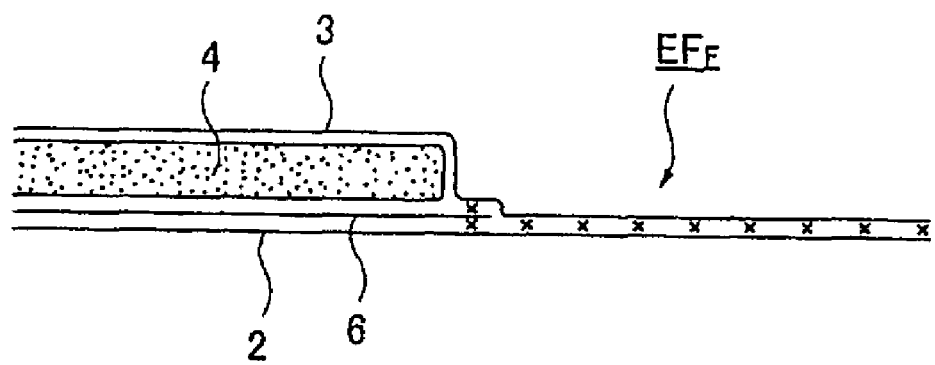
FIG. 15 A section showing a modification of the front-side end flap portion $EF_F$.
Figure 16:
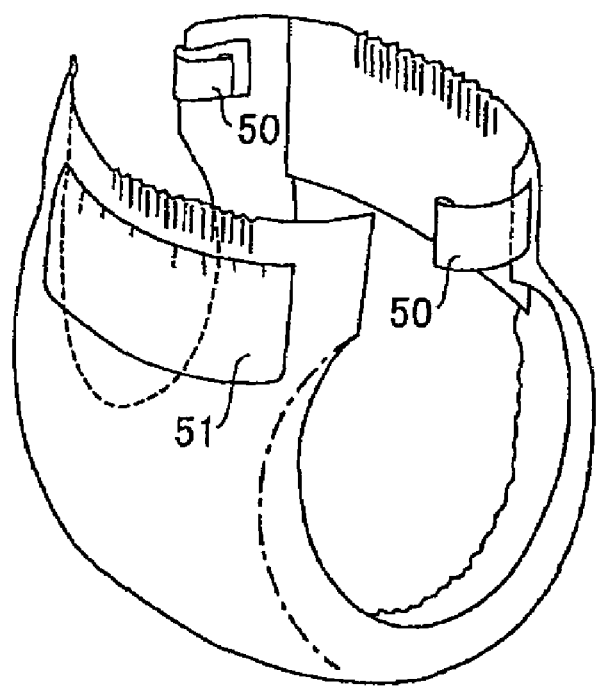
FIG. 16 A perspective view of the disposable paper diaper of the prior art.

(3) In the aforementioned mode of embodiment, the front-side end flap portion $EF_F$ has the three-layered constitution of the liquid-permeable top sheet 3, the leakage-preventing sheet 6 and the outer-face back sheet 2. As shown in FIG. 15, however, the aforementioned leakage-preventing sheet 6 may be so extended slightly to the outer side from the front end edge of the absorbing member 4 as is joined to the liquid-permeable top sheet 3, and the aforementioned front end flap portion $EF_F$ may be substantially constituted of the liquid-permeable top sheet 3 and the outer-face back sheet 2. In this case, the leakage-preventing sheet 6 is not interposed to improve the flexibility (or softness) thereby to facilitate the folding-back, and the wearability is not deteriorated even in case the diaper is folded back.

(4) In the aforementioned mode of embodiment, the lines 16 are formed as the guide indication of the folding positions, but any indication is acceptable if it guides the folding positions with marks, patterns or numerals.

The invention claimed is:

1. A disposable diaper comprising: an absorbing member; a liquid-permeable top sheet covering the surface side of said absorbing member; a leakage-preventing sheet covering the backside of said absorbing member; an outer-face back sheet made of a nonwoven fabric and disposed on the outer face side of said leakage-preventing sheet; and mechanical joining type fastening tapes disposed on the two side portions of the back side of the diaper, wherein said fastening tapes are brought, when the diaper is worn, into direct engagement with the surface of said outer-face back sheet, and further comprising a front-side end flap portion and a back-side end flap portion having no absorbing member, respectively, at the front and back end portions in the longitudinal direction of the diaper;

wherein at least said front-side end flap portion is formed over at least a length range of 5% or more of the diaper product in the longitudinal direction from the diaper end edge;

wherein said front-side end flap portion has no elastically extendible member arranged, but the aforementioned leakage-preventing sheet extends slightly to the outer-side from the front-side end edge of the absorbing member and is joined to the aforementioned liquid permeable top sheet;

wherein the aforementioned front-side end flap is substantially composed of a liquid-permeable top sheet and the outer-face back sheet so that said front-side end flap portion can be longitudinally folded at an arbitrary position;

wherein the front-side end flap, along an entire waist length of the front-side end flap, has a thickness, defined only by the thickness of the liquid-permeable top sheet and the outer-face back sheet at a portion distal to a distal fold of the front-side end flap;

wherein said front-side end flap portion is provided on its outer-face side with a folding position guide indication provided by printing and visible from the outside; and wherein said outer-face back sheet is made of a nonwoven fabric manufactured by an air-through method, in which hot air is fed in a drum transfer process during nonwoven fabric manufacturing to melt fibers thermally to each other, and wherein the drum contacting face side is positioned to become the diaper's inner side and have a flat face, and the drum non-contacting side is positioned to become the diaper's outer side and have a bulky face.

2. A disposable diaper as set forth in claim 1, wherein said front-side end flap portion is provided with a plurality of linear or band-shaped portions having a degree of rigidity different from that of said front-side end flap portion, at an interval longitudinally of the diaper and along the widthwise direction of the diaper.

* * * * *